(12) United States Patent
Rolfes (10) Patent No.: US 9,681,924 B2
(45) Date of Patent: Jun. 20, 2017

(54) SKULL CLAMP WITH IMPROVED POSITIONABILITY AND CLEANING CAPABILITY

(76) Inventor: Sean Rolfes, Cincinnati, OH (US)

( * ) Notice: Subject to any disclaimer, the term of this patent is extended or adjusted under 35 U.S.C. 154(b) by 1905 days.

(21) Appl. No.: 12/749,926

(22) Filed: Mar. 30, 2010

(65) Prior Publication Data
US 2010/0249780 A1 Sep. 30, 2010

Related U.S. Application Data

(60) Provisional application No. 61/211,510, filed on Mar. 31, 2009.

(51) Int. Cl.
*A61F 5/00* (2006.01)
*A61B 90/14* (2016.01)
*A61B 17/00* (2006.01)
*A61B 90/00* (2016.01)

(52) U.S. Cl.
CPC .... *A61B 90/14* (2016.02); *A61B 2017/00407* (2013.01); *A61B 2090/0813* (2016.02)

(58) Field of Classification Search
CPC ....... A61B 17/64–17/663; A61B 90/14; A61B 2090/0813; A61B 17/02–17/0293
USPC ............. 606/53–59, 324, 277, 86 R, 87–91
See application file for complete search history.

(56) References Cited

U.S. PATENT DOCUMENTS

| | | | |
|---|---|---|---|
| 4,169,478 A * | 10/1979 | Hickmann | 606/151 |
| 5,254,079 A | 10/1993 | Agbodoe et al. | |
| 5,269,034 A | 12/1993 | Day et al. | |
| 5,276,927 A | 1/1994 | Day | |
| 5,318,509 A | 6/1994 | Agbodoe | |
| 5,537,704 A * | 7/1996 | Dinkler | 5/622 |
| 5,630,820 A * | 5/1997 | Todd | 606/90 |
| 6,381,783 B2 * | 5/2002 | Reinhardt et al. | 5/622 |
| 6,629,982 B2 | 10/2003 | Day et al. | |
| 7,229,451 B2 * | 6/2007 | Day et al. | 606/130 |
| 7,507,244 B2 | 3/2009 | Dinkler | |
| 7,618,420 B2 * | 11/2009 | Collazo | 606/87 |
| 7,661,162 B2 * | 2/2010 | Soerensen et al. | 5/622 |
| 7,882,583 B2 * | 2/2011 | Skripps | 5/621 |
| 2009/0118774 A1 * | 5/2009 | Miller, III | 606/324 |

OTHER PUBLICATIONS

"Hinge" Macmillan dictionary. Maximillian publishers Limited. accessed Jan. 14, 2013 http://www.macmillandictionary.com/dictionary/american/hinge-joint.*

* cited by examiner

*Primary Examiner* — Jan Christopher Merene
*Assistant Examiner* — Steven Cotroneo
(74) *Attorney, Agent, or Firm* — Wood Herron & Evans LLP (57) ABSTRACT

A three-pin skull clamp, including a U-shaped frame defined by an interconnectable base piece with a slot that receives the ratchet arm of a ratchet piece, also includes a plate movably connected to the base piece, thereby to permit inspection and cleaning of the slot which receives the ratchet arm. To increase the adjustability of the ratchet piece relative to the base piece, the base piece includes at least two pawls with offset engagement teeth, preferably with the offset equal to half the pitch of ratchet teeth located along the ratchet arm. This feature facilitates positioning of the skull clamp relative to a patient, and is particularly beneficial for radiolucent skull clamps.

25 Claims, 12 Drawing Sheets

SKULL CLAMP WITH IMPROVED POSITIONABILITY AND CLEANING CAPABILITY

RELATED APPLICATION

The present application claims priority to U.S. Ser. No. 61/211,510, filed Mar. 31, 2009, the disclosure of which is hereby incorporated by reference herein in its entirety.

FIELD OF THE INVENTION

This invention relates generally to a skull clamp for cranial fixation, and more particularly, to a radiolucent skull clamp with improved adjustability relative to a patient's head and greater capability for cleaning and inspection.

BACKGROUND OF THE INVENTION

Supports for securing the head of a patient during surgical or radiological procedures are known in the art. Such supports are typically adjustable so the head of the patient may be secured in different positions for different radiological views, or to facilitate access to a patient's head during a surgical procedure. Such head supports typically include a base unit that mounts to the head end of a patient support table. The base unit has a horizontal cross bar that supports one or more adapters, which in turn support a skull clamp that holds the patient's head. The skull clamp and the one or more intervening adapters or other members enable operating room attendants to adjust the height, distance, and orientation of the skull clamp with respect to the end of the table, to hold the patient's head in a desired position. An exemplary support system includes a base unit, a skull clamp, and a swivel adapter.

Many skull clamps on the market use a two piece U-shaped construction with one end of the U-shape holding one inwardly directed pin and the other end holding a rocker arm that supports two spaced head holding pins. The two pieces are referred to in this disclosure as the base piece and the ratchet piece. At the closed end of the U-shape, the ratchet piece has a ratchet arm that slides through a slot or passage formed in the base piece. A locking mechanism mounted to the base piece relative to the slot engages the ratchet aim to prevent it from backing out. The slot through the base piece is only accessible from either end. Because the slot is several inches long and only wide enough to accept the complementary shaped ratchet arm, visual access to the interior surfaces of the slot or to the ratchet locking mechanism is limited. Thus, the shape and the interconnection of the slot and the ratchet arm limit the ability to clean or to inspect the slot. Yet, the use of such a skull clamp in a surgical environment practically assures that fluids of one type or another, or other substances, will inevitably find their way to the inside surfaces of the slot. Thus, there is a need for a design that facilitates cleaning and inspection of the inside surfaces of the slot and the locking mechanism.

Typically, head supports such as skull clamps have been fabricated from stainless steel or other metals. However, head supports made of metal components are radiopaque to x-rays, and thus produce artifacts in the x-rays taken when the skull clamp is interposed between the x-ray source and the x-ray film. These artifacts are created by the metal components, which block the path of the x-rays as they travel from the source to the film. More particularly, the areas of the x-ray film where the x-rays are blocked by the metal will be unexposed, and will appear as artifacts in the developed x-ray picture. These artifacts diminish the usefulness of the developed x-ray picture because they obscure the image of a portion of the head that normally would be viewable, absent the obscuring metal portion of the head support.

For these reasons, head supports can be made from radiolucent materials that permit x-rays to pass therethrough, thereby to reduce artifacts. An example of a known radiolucent skull clamp is shown in the Day, et al. U.S. Pat. No. 5,276,927, owned by the assignee of this application. This '927 patent discloses a radiolucent head support with a radiolucent skull clamp secured to the head support. When using this structure, the radiolucent material results in fewer artifacts in the developed x-ray picture.

Another example of a known radiolucent skull clamp is shown in Dinkier, U.S. Pat. No. 5,537,704, also assigned to the assignee of this application. Similar to the skull clamp structure described above, it discloses a radiolucent head clamp having a U-shaped frame with a fixed head-engaging pin at one open end of the U-shape and a pair of head-engaging pins on the opposite end of the U-shape. The closed end of the U-shape of the clamp has a radiolucent rotation mechanism for adjusting the angular position of the pair of head-engaging pins and a radiolucent translation mechanism for linearly moving the pair of head-engaging pins with respect to the fixed head-engaging pin.

Generally, the skull clamps currently on the market use a ratchet and pawl mechanism to control the position of the ratchet arm relative to the base piece. More particularly, ratchet teeth along the ratchet arm engage a pawl housed inside the slot of the base piece. The pawl is biased into engagement with the ratchet teeth, so that once a ratchet tooth moves past the pawl it cannot be moved in the other direction, until a biased plunger mounted on the base piece is pulled against its biasing force to move the pawl away from the ratchet teeth, thereby to allow the ratchet arm to be removed from the slot. The distance between adjacently located ratchet teeth is called the pitch. As the ratchet arm moves further into the slot, the pawl engages another ratchet tooth each time the ratchet arm travels into the slot a distance of one complete ratchet tooth, i.e., the distance of the pitch. A neurosurgical skull clamp device that uses a sliding ratchet mechanism and single pawl is described in U.S. Pat. No. 3,835,861. Each of the three above-cited patents is incorporated by reference herein, in its entirety.

With this type of structure, the distance between ratchet teeth should be sufficient enough to provide robust teeth, so as to assure a strong connection for the head holding components. However, the larger the teeth, the greater the pitch (distance between two ratchet teeth), and the greater the pitch, the lower the adjustability of the ratchet piece relative to the base piece.

Greater adjustability could be achieved with finer teeth. However, finer teeth would likely be more readily damaged over the course of normal use. And for some materials, including the plastic-type radiolucent materials used to make a radiolucent skull clamp, finer teeth would be structurally susceptible to breakage.

Thus, while the x-ray pictures produced by radiolucent head supports have fewer artifacts, such head supports can present other problems. For instance, compared to metals, radiolucent materials are not as well suited for certain components in the adjusting mechanisms of the above described skull clamp design. If such components are made from a plastic-type radiolucent material, the clamping forces could be reduced over time, because the plastic radiolucent components can be susceptible to deformation, and can lose their initial geometry. These conditions could eventually result, over time, in a loss of dimensional precision for the clamp. As a result, the operation and fixation of the two skull clamp frame pieces, and hence the positioning of the patient's head, could become inconsistent and unsatisfactory.

Thus, there is a need to assure a long-lasting, consistent and robust connection of the two pieces of a skull clamp, particularly for a skull clamp that is made from radiolucent materials.

SUMMARY OF THE INVENTION

The present invention meets these needs by incorporating into the base piece of a skull clamp a movably connected plate, the plate being movable relative to the base piece to open up and to close off access to the slot that receives the ratchet arm of the ratchet piece of the skull clamp, thereby to allow and to facilitate inspection and cleaning of the slot. Preferably, the plate has first and second ends, and the first end is hingedly connected to the base piece by a pin. The second end mates with the base piece to close off access to the slot, when the ratchet arm is advanced into the slot. The second end is adapted to be pulled to hingedly open the plate, when the ratchet arm is not extended into the slot of the base piece.

According to a more detailed aspect of the disclosure, the plate hingedly moves about the pin, and the plate cooperates with a ratchet locking mechanism to engage the ratchet teeth of the ratchet arm to lock the ratchet piece in a desired location relative to the base piece.

In an alternative approach to this embodiment, which also facilitates cleaning and inspection, the plate is removably connected to the base piece by sliding it along opposing channels located near the bottom of the slot.

According to yet another aspect of the invention, the disclosed skull clamp allows better control and adjustability of the ratchet arm, and requires less force to apply the clamp to the patient's head, due to the use of a multiple-pawl mechanism for engaging the ratchet teeth. The multiple-pawl mechanism includes a first pawl and a second pawl that have engagement teeth that are offset by a distance that is a fraction of the pitch distance of the ratchet teeth, such that the ratchet arm may be engaged more than once as it travels the pitch distance into the slot. Each of the first and second pawls can have one tooth, two teeth, or more. This feature is particularly advantageous when the skull clamp is made of radiolucent material.

According to a first preferred embodiment of the disclosure, the plate and the pawls rotate together. Further, the plate carries a plunger (with a plunger handle and a plunger body), which cooperates with the pawls to enable them to be biased into contact with the ratchet teeth, or removed therefrom, by pulling the plunger away from the base piece and against the biasing force. This pulling allows the ratchet arm to be removed from the slot so that the two pieces disconnect. In one sense, with this approach the improved adjustability feature can also be considered to form part of the cleaning/inspecting feature, in that the offset pawls mount to the base piece so as to be rotatable about the same pin that defines the axis of hinged connection for the plate.

According to still another aspect of this particular embodiment, each of the pawls includes a spring, preferably an integral spring arm, that supplies the biasing force that biases the engagement teeth of the pawl into engagement with the ratchet teeth. This biasing force also holds the plunger handle against the base piece.

A second preferred embodiment of the adjustability feature contemplates pawls that are completely independent of the removable plate. For instance, opposing pawls can be located on opposite sides of the base piece, and adapted to interact with corresponding opposing sets of engagement teeth. In this second preferred embodiment, the plate slidably removes from the base piece, and the operation of the plate is completely independent of the two opposing pawls. As a further alternative to this approach, the two pawls could be on the same side of the base piece, so long as they are offset.

Other features and advantages of the present invention will become more apparent from the following detailed description of the invention, when taken in conjunction with the accompanying exemplary drawings.

DETAILED DESCRIPTION OF THE INVENTION

Figure 1:
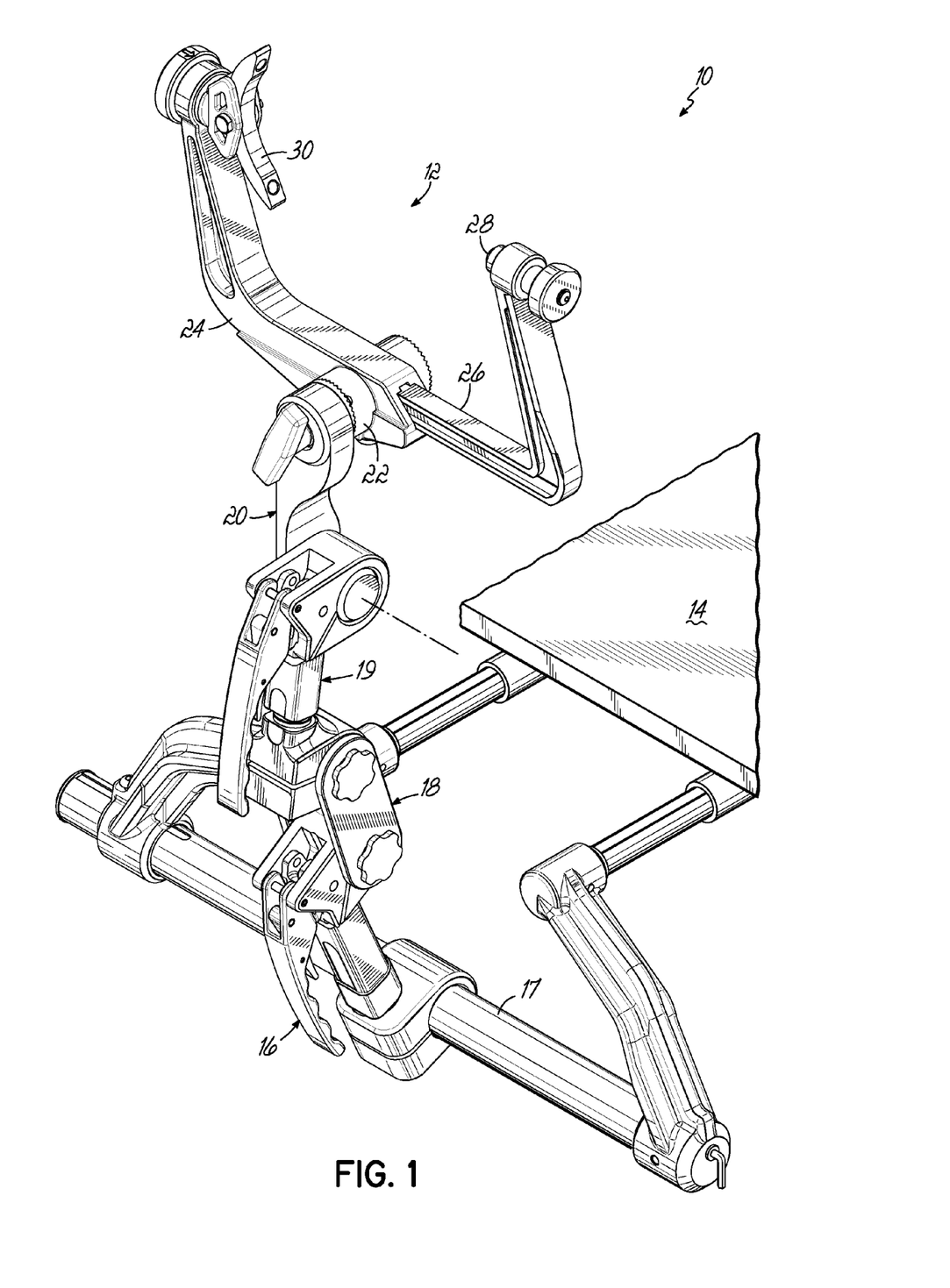
FIG. 1 is a perspective view of a conventional three-pin skull clamp connected to a patient table, to exemplify the use and environment of one type of skull clamp to which the present invention is applicable.

FIG. 1 shows a head support system 10 for supporting a patient (not shown) via a skull clamp 12 at the end of a surgical table 14. According to the arrangement of components shown in FIG. 1, in additional to the skull clamp 12, the head support system 10 includes a base unit 16, which includes a crossbar 17, and first, second, and third adapters 18, 19, and 20, respectively, which operatively connect the skull clamp 12 to the base unit 16. Those skilled in the art will readily appreciate that in some situations only one, or possibly two, adapters may be used to adequately support the patient relative to the table 14.

The skull clamp 12 includes a hub 22 with a starburst connection that connects to the uppermost adapter 20. The skull clamp 12 of FIG. 1 includes a base piece 24 and a ratchet piece 26 which, when connected, generally define an upwardly opening U-shape. The ratchet piece 26 supports a single pin holding structure 28 at one open end of the U-shape, while the base piece 24 supports a rocker arm 30 capable of holding two spaced skull pins at an opposite end of the U-shape.

Figure 2:
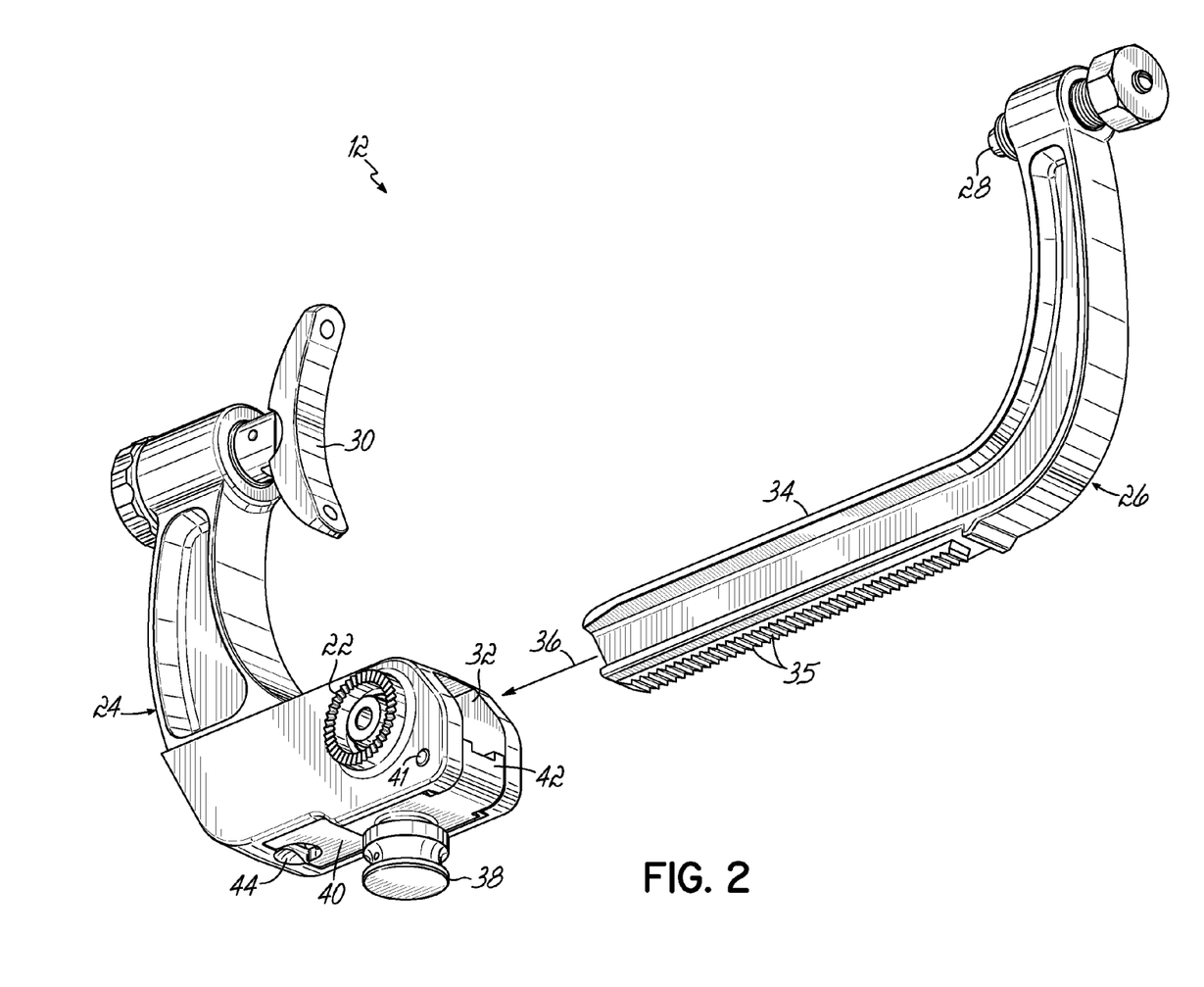
FIG. 2 is a disassembled perspective view of a skull clamp constructed according to a first preferred embodiment of the disclosure.

FIG. 2 shows this structure in greater detail, with base piece 24 having a slot 32 formed therein for receiving a ratchet arm 34 of the ratchet piece. The ratchet arm 34 includes the plurality of ratchet teeth 35. The slot 32 is sized to receive the ratchet arm 34, as shown by directional arrow 36. When the ratchet arm 34 moves into the slot 32, the ratchet teeth 35 engage the internal surface in the slot 32, so as to prevent the ratchet arm 34 from being removed from the slot 32. A plunger handle 38 mounts to the base piece 24, and forms part of the structure within the slot 32 that cooperates with the ratchet teeth 35 to enable the ratchet arm 34 to move further into the slot 32, but which also prevents the ratchet arm 34 from removing outwardly from slot 32, at least until the plunger handle 38 is pulled away from the base piece 24. The plunger handle 38 is preferably biased to a closed position, as shown in FIG. 2, so as to cooperate with internal structure of the base piece 24 to engage against the ratchet teeth 35, as will be described in more detail below.

Figure 4A:
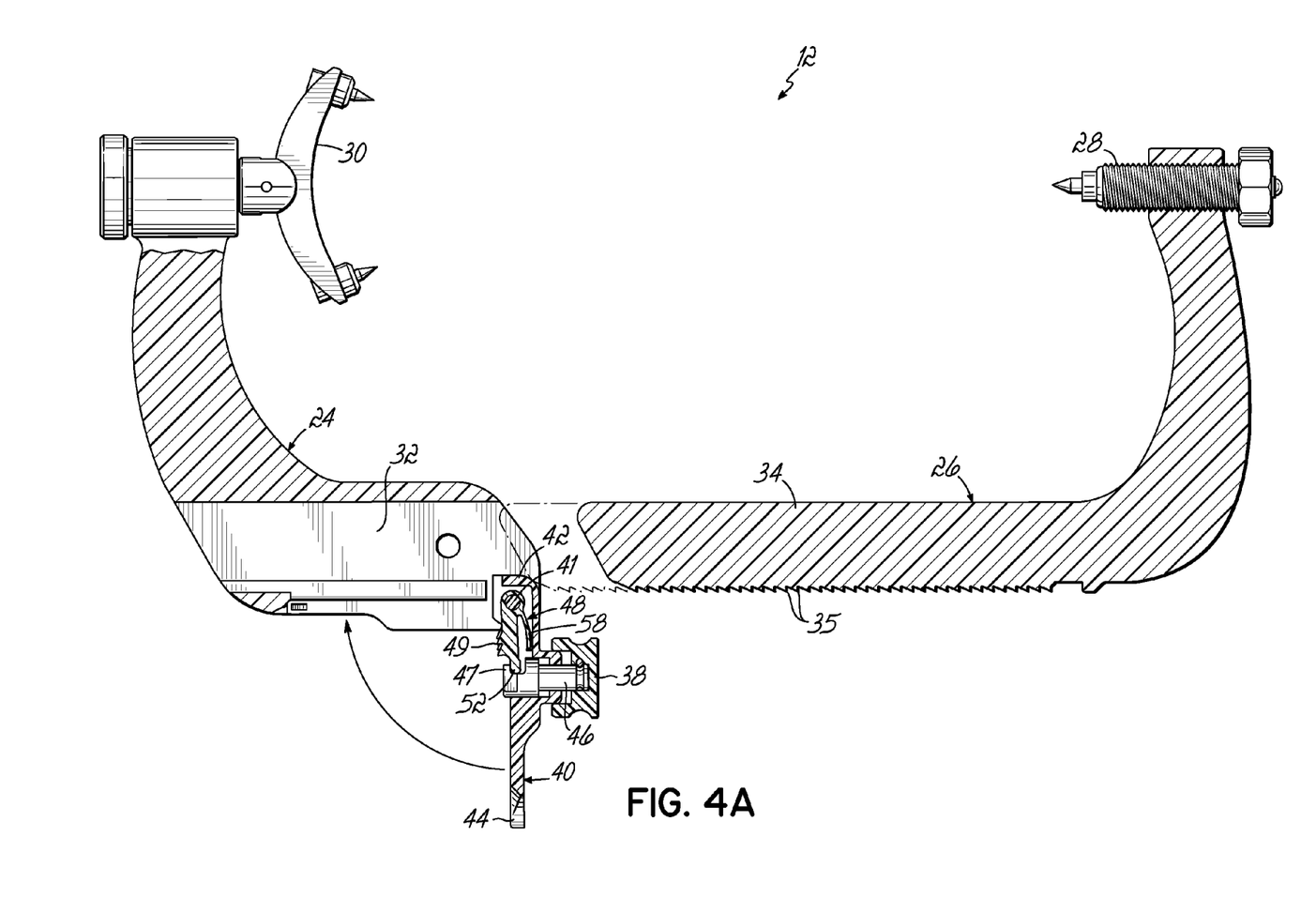
FIG. 4A is a side view of the disassembled skull clamp shown in FIGS. 2 and 3, with the plate hingedly moved to an open position.

FIG. 2 also shows a plate 40 which is hingedly connected to the base piece 24 via a pin 41. The plate 40 is hingedly connected to the base piece 24 at a first end thereof 42, and also has a second end 44 that cooperates with the structure of base piece 24, as for instance by a snap connection, or other suitable mechanical connection, but enables the plate 40 to be pulled downwardly (downwardly as shown in FIG. 4A) from the base piece 24 thereby to open access into the slot 32. Because the plunger handle 38 is secured to the plate 40, it hingedly moves with the plate 40 with respect to base piece 24, about the axis defined by pin 41.

Figure 3:
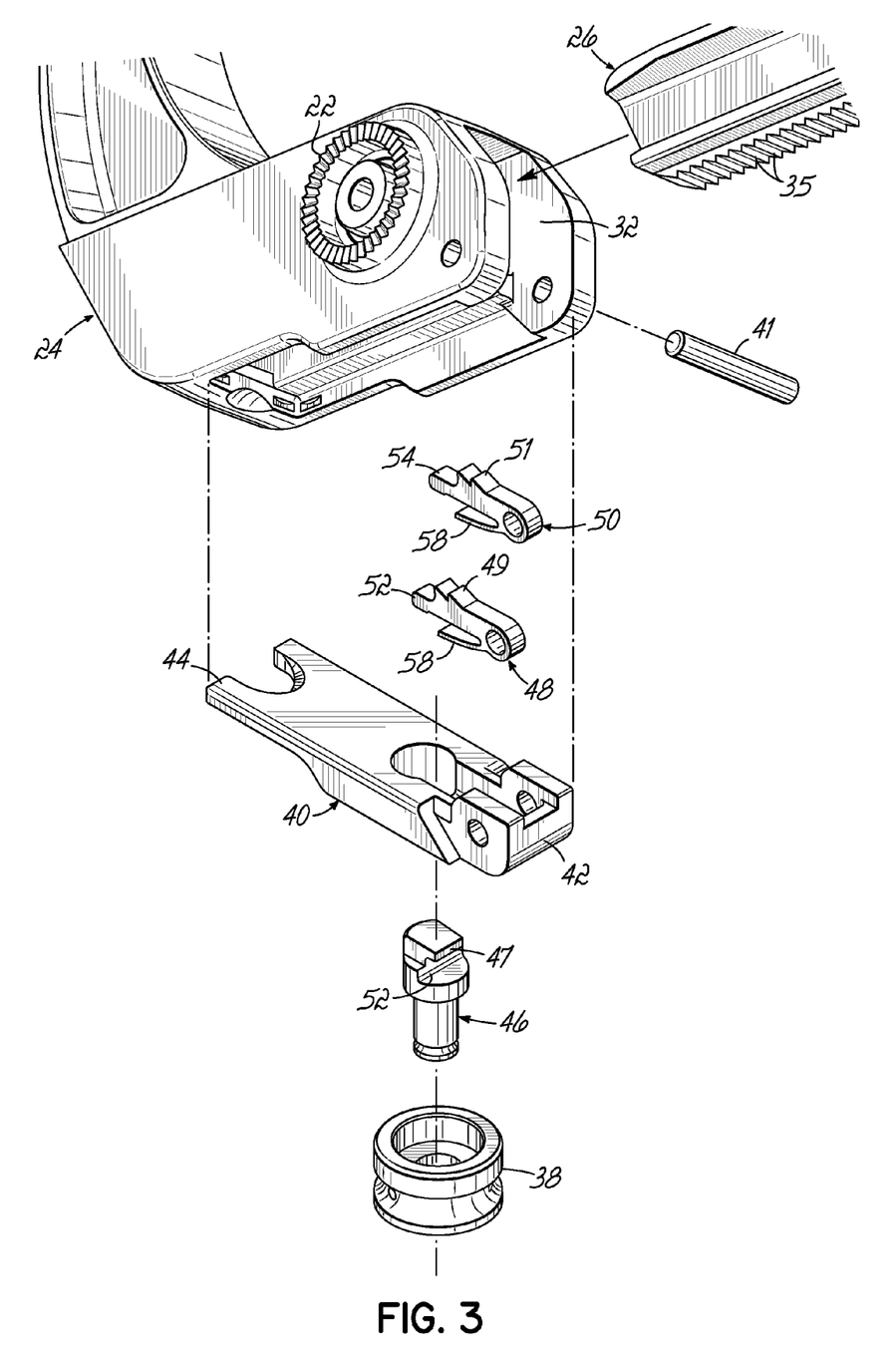
FIG. 3 is an enlarged, disassembled view of a plate that hingedly connects to a base piece of a skull clamp constructed according to the first preferred embodiment of the disclosure.

FIG. 3 shows, in a disassembled condition, the components of the base piece 24 that cooperate with the plate 40. More particularly, the plunger handle 38 connects to a plunger body 46. The plunger body 46 includes a recess 47 to be described in greater detail with respect to FIGS. 4A, 4B, and 4C. Although not shown in detail in FIG. 3, the plunger body 46 cooperates with a first pawl 48, and the first pawl 48 includes at least one engagement tooth 49 that is shaped complementary to the ratchet teeth 35. Preferably, the at least one first engagement tooth 49 includes two spaced engagement teeth, with a pitch equal to that of the ratchet teeth 35. Those skilled in the art will readily appreciate that additional complementary shaped engagement teeth could be used, if desired. A second pawl 50 resides adjacent to the first pawl 48, and includes at least one second engagement tooth 51 that is also shaped complementary to the ratchet teeth 35. Preferably, the at least one second engagement tooth 51 also comprises two spaced engagement teeth, with a pitch equal to the pitch of the ratchet teeth 35.

FIG. 4A shows the orientation of the base piece 24 and ratchet piece 26 prior to extension of the ratchet arm 34 into the slot 32, but with plate 40 hingedly moved to an open position, thereby to open up access to the inside of the slot 32. As shown in FIG. 4A, the recess 47 of the plunger body 46 holds an outermost end 52 of first pawl 48 and also an outermost end 54 of second pawl 50 (although outermost end 54 cannot be seen in FIG. 4A). With this arrangement, hinged movement of plate 40 with respect to base piece 24 about an axis defined by pin 41 carries the plunger handle 38 and the plunger body 46, while at the same time pivoting the first pawl 48 and the second pawl 50 relative to the pin 41.

With plate 40 hingedly moved to the open position relative to pin 41, the user has easy access into slot 32, to enable relatively easy cleaning and/or inspection of the slot 32. This enables the operator to remove debris therefrom, or to wipe the inside surfaces clean. Also, when the plate 40 is in the open position, the ratchet piece 26 cannot be inserted into the opening.

Figure 4B:
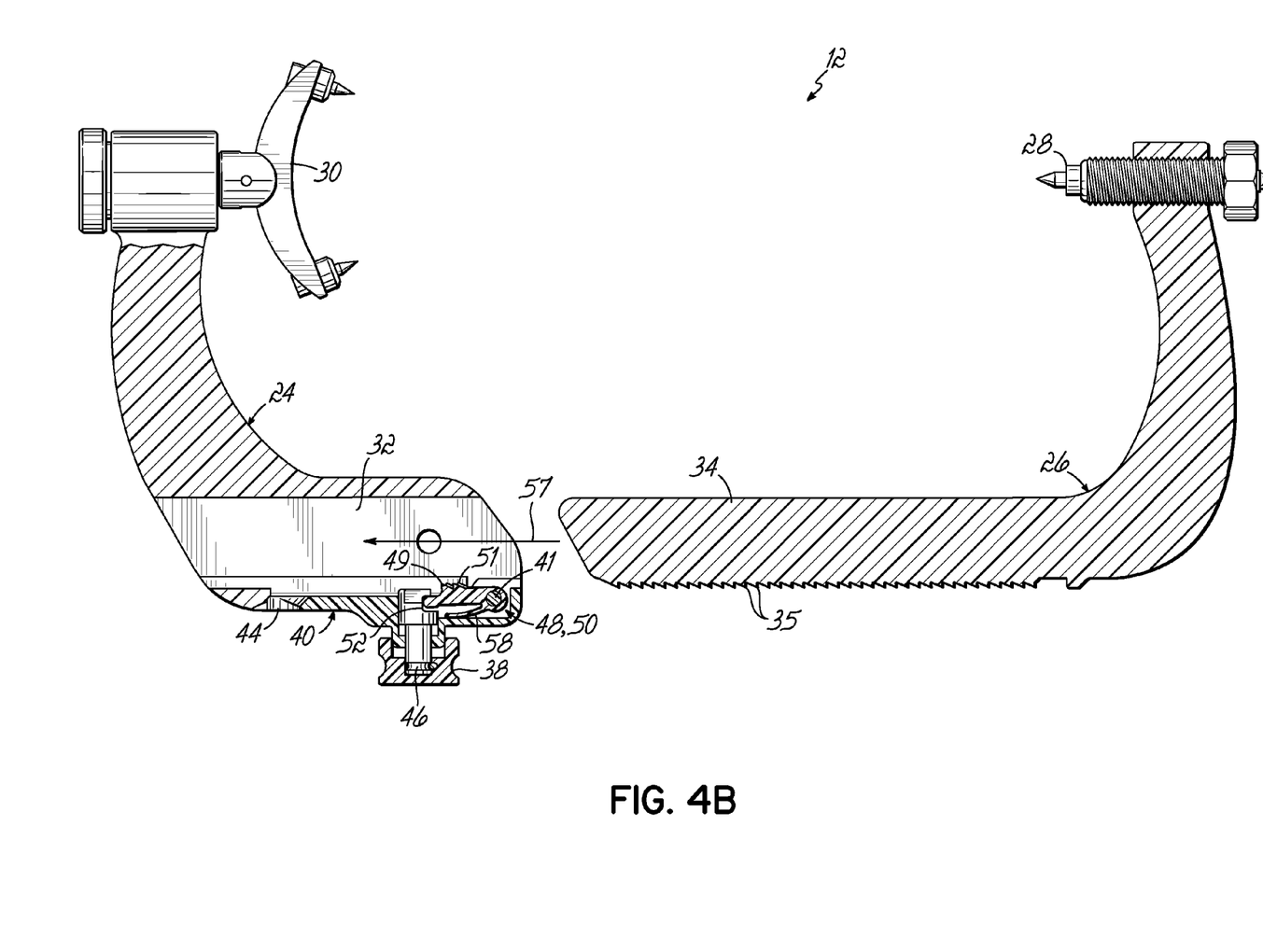
FIG. 4B is a side view of the disassembled skull clamp shown in FIGS. 2 and 3, with the plate hingedly moved to a closed position.

FIG. 4B shows the plate 40 in a closed position, so that the slot 32 is entirely closed off, except at its outermost ends, and the slot 32 is ready to receive the ratchet arm 34. With the plate 40 in the closed position, the first engagement teeth 49 of first pawl 48 reside in a position so as to engage the ratchet teeth 35 of the ratchet arm 34, as the ratchet piece 36 moves in the direction shown via directional arrow 57. Similarly, second engagement teeth 51 are also located and oriented in a position so as to engage the ratchet teeth 35 as ratchet arm 34 moves into the slot 32. FIG. 4B shows that, in this position, a spring 58, in this embodiment an integral spring-arm, acts on first pawl 48 and on the inside surface of the plate 40 so as to hold the first engagement teeth 49 biased in an uppermost position (upper with respect to FIG. 4B).

Figure 4C:
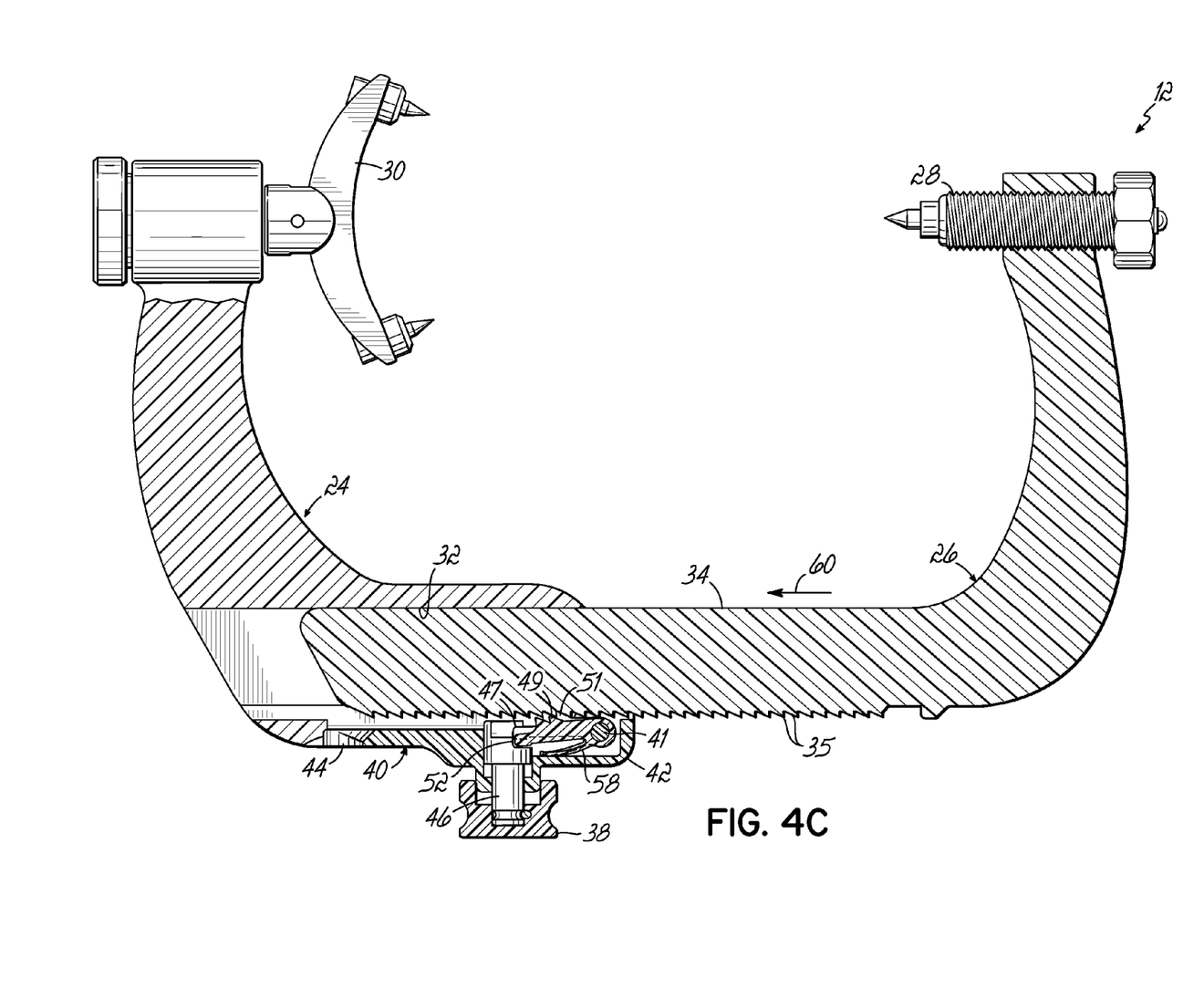
FIG. 4C is a side view similar to FIGS. 4A and 4B, but with the ratchet arm extended into the slot of the base piece.

FIG. 4C shows the same components in the same relative positions, except that ratchet arm 34 has been moved further within slot 32, as shown via directional arm 60, which is the leftward direction as shown in FIG. 4C. As ratchet arm 34 moves into slot 32 the ratchet teeth 35 engage first engagement teeth 49. The force of the insertion of ratchet arm 34 causes the teeth 35 to engage the first engagement teeth 49, and thereby cause the first pawl 48 to rotate slightly in a counterclockwise direction relative to pin 41, against the biasing force supplied by integral spring arm 58. As one of the ratchet teeth 35 moves past the tip of one of the engagement teeth 49, the clockwise directed bias supplied by spring 58 causes the first pawl 48 to rotate slightly in a clockwise direction relative to pin 41, until the next of the ratchet teeth 35 moves past, whereupon first pawl 48 again moves counterclockwise with respect to pin 41 because of the force applied by the ratchet teeth 35. This continues so long as the ratchet arm 34 moves into slot 32, not only with respect to first pawl 48 and first engagement teeth 49, but also with respect to second pawl 50 and second engagement teeth 51.

Figure 5A:
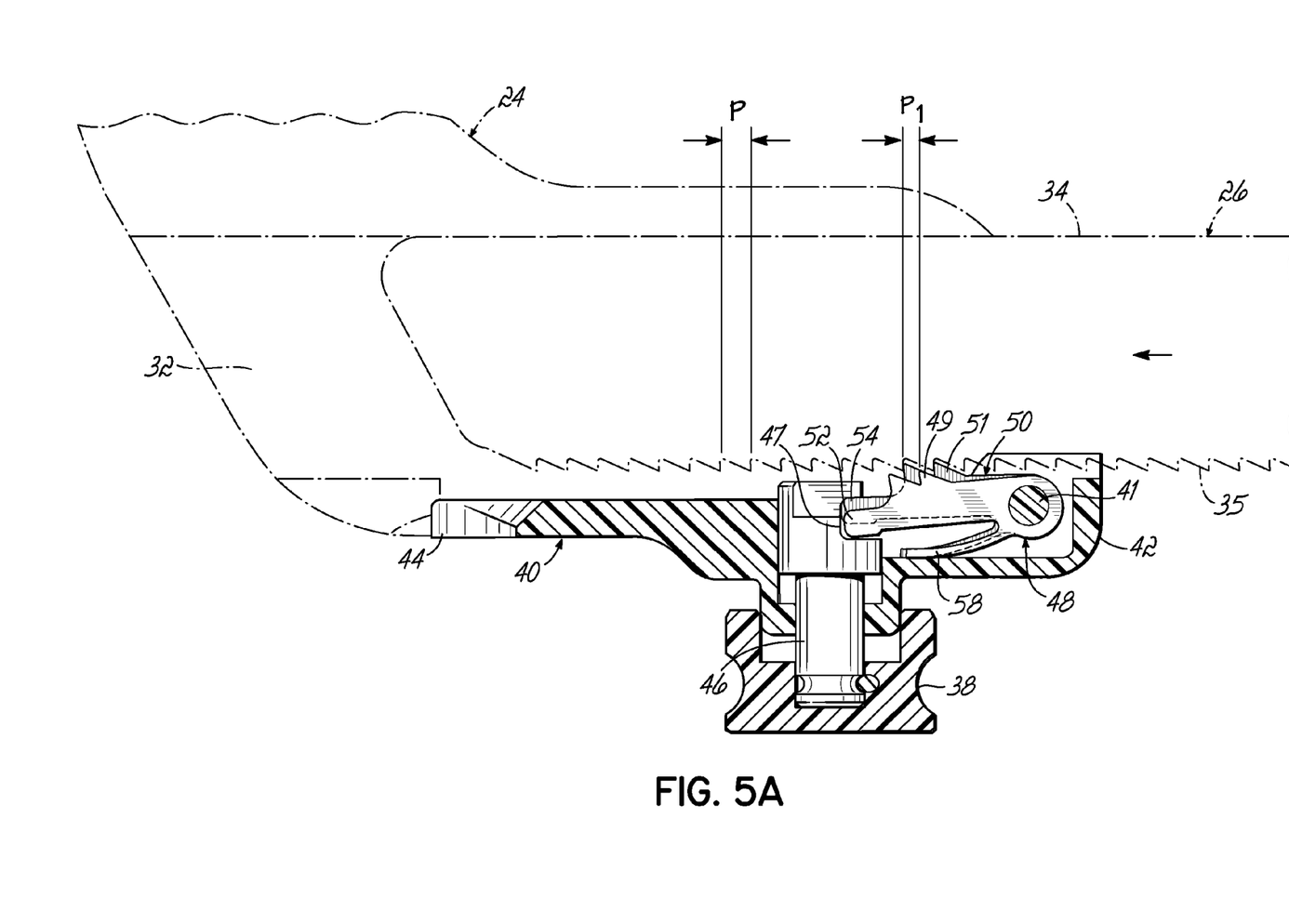
FIG. 5A is an enlarged side view of the plate and the accompanying plunger and pawl structure, wherein the ratchet arm is extended into the slot of the base piece, with the engagement teeth of the distal pawl shown in engagement with the ratchet teeth.

FIG. 5A shows a view similar to that of FIG. 4C, but with the plate 40 and the components that interact therewith shown in an enlarged form. Because of the enlarged view, FIG. 5A shows the offset relationship between first pawl 48 and second pawl 50. More particularly, FIG. 5A shows the second engagement teeth 51 residing in engagement with two of the engagement teeth 35, while the first engagement teeth 49 have moved downwardly (counterclockwise) in FIG. 5A, due to counterclockwise rotation about pin 41 caused by leftward movement of the engagement teeth 35. The movement of first pawl 48 is caused by the angled surface in the ratchet teeth 35. There is a ramping, or a camming, action when the ratchet arm 34 moves into the slot 32.

FIG. 5A also shows the pitch, designated by P, which refers to the space between the ratchet teeth 35. FIG. 5A also shows the offset distance, designated by $P_1$, between first engagement teeth 49 and second engagement teeth 51. Preferably offset distance $P_1$ is about half the pitch P of the ratchet teeth 35, although any one of a number of offset distances would also work, even an offset distance greater than the pitch.

Figure 5B:
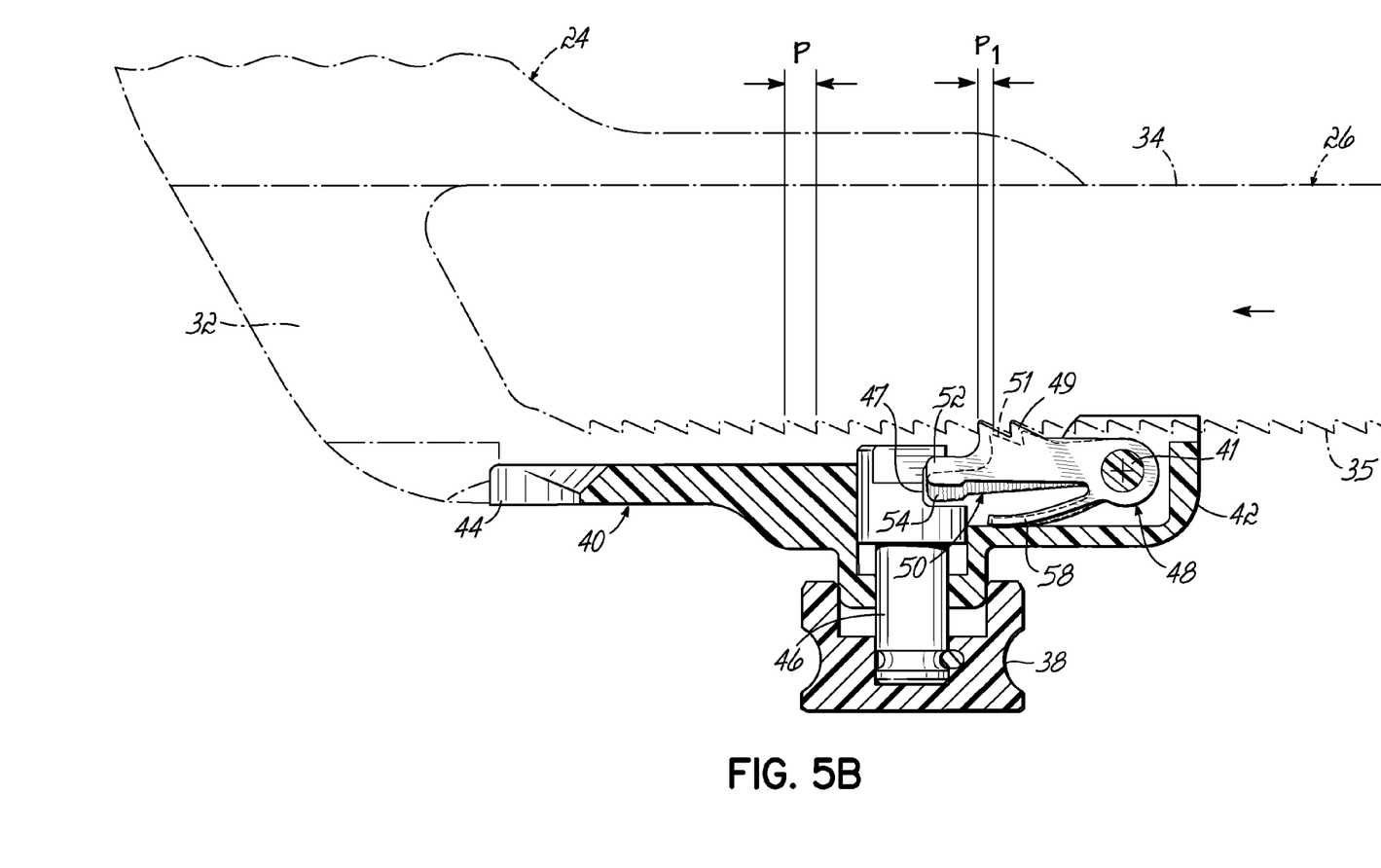
FIG. 5B is an enlarged side view, similar to FIG. 5A, but with the engagement teeth of the closest pawl shown in engagement with the ratchet teeth.

FIG. 5B is very similar to FIG. 5A, except that the ratchet arm 34 has been moved further into the slot 32, so that the ratchet teeth 35 have caused the second engagement teeth 51 to move downwardly, counterclockwise, against the respective biasing force, while first engagement teeth 49 have moved upwardly, i.e., clockwise relative to pin 41, into engagement with the ratchet teeth 35.

Figure 5C:
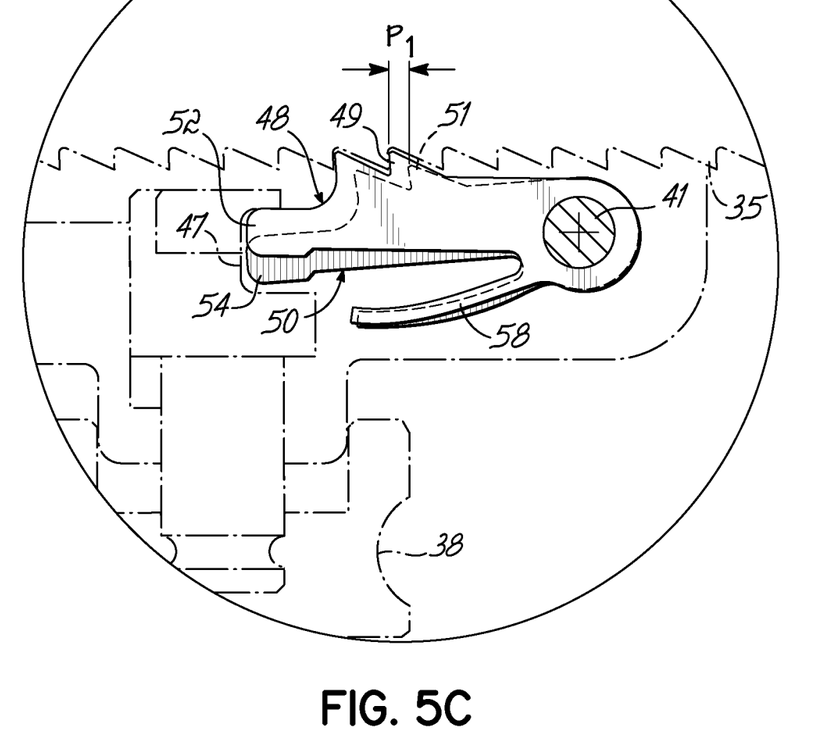
FIG. 5C is a side view, similar to FIGS. 5A and 5B, showing the offset distance between the engagement teeth of the first end second pawls.

FIG. 5C shows an enlarged, more detailed view of the view shown in FIG. 5B, but with the first pawl 48 shown in the foreground, and the second pawl 50 shown in the background. FIG. 5B shows the relative positions of these two pawls 48, 50, and the first engagement teeth 49 and second engagement teeth 51, respectively, relative to the ratchet teeth 35. Although as shown in these Figures the offset distance $P_1$ is about half the pitch P of the ratchet teeth 35, those skilled in the art will readily appreciate that the offset distance may vary, so long as it is some distance less than pitch P. This multiple pawl structure, with offset engagement teeth, enhances the adjustability of the skull clamp 12 by enabling the ratchet piece 26 to be held fixed relative to base piece 24 in essentially twice as many positions. This creates the same effect as having ratchet teeth of smaller, i.e., finer size and shape. Yet this additional adjustability is achieved without reducing the size of either the ratchet teeth 25 or the engagement 49, 51. Thus, the robustness of the connection is not sacrificed. This feature is particularly advantageous if the components of the skull clamp 12 are made of radiolucent material, because with such materials it is even more important to maintain a sufficient size, shape, and pitch for the ratchet teeth 35 and the engagement teeth 49, 51 which engage the ratchet teeth 35.

Also, because of the shape of the second end 42 relative to the ratchet teeth 35, the plate 40 cannot be hingedly opened when the ratchet arm 34 is located inside the slot 32. Rather, the ratchet arm 34 must first be withdrawn from the slot 32, via manipulation of the plunger handle 38 against the biasing force applied by integral spring arm 58. This is shown in FIG. 4A, which shows that the profiles of the second end 42 of the plate 40 and the ratchet teeth 35 of the ratchet arm 34 overlap to prevent such hinged opening. Because of the way the plate 40 interacts with the ratchet teeth 35, i.e., via this structural overlap, the second end 42 serves as a safety feature for skull clamp 12. This feature is particularly helpful when the skull clamp 12 is made of radiolucent components.

Figure 6:
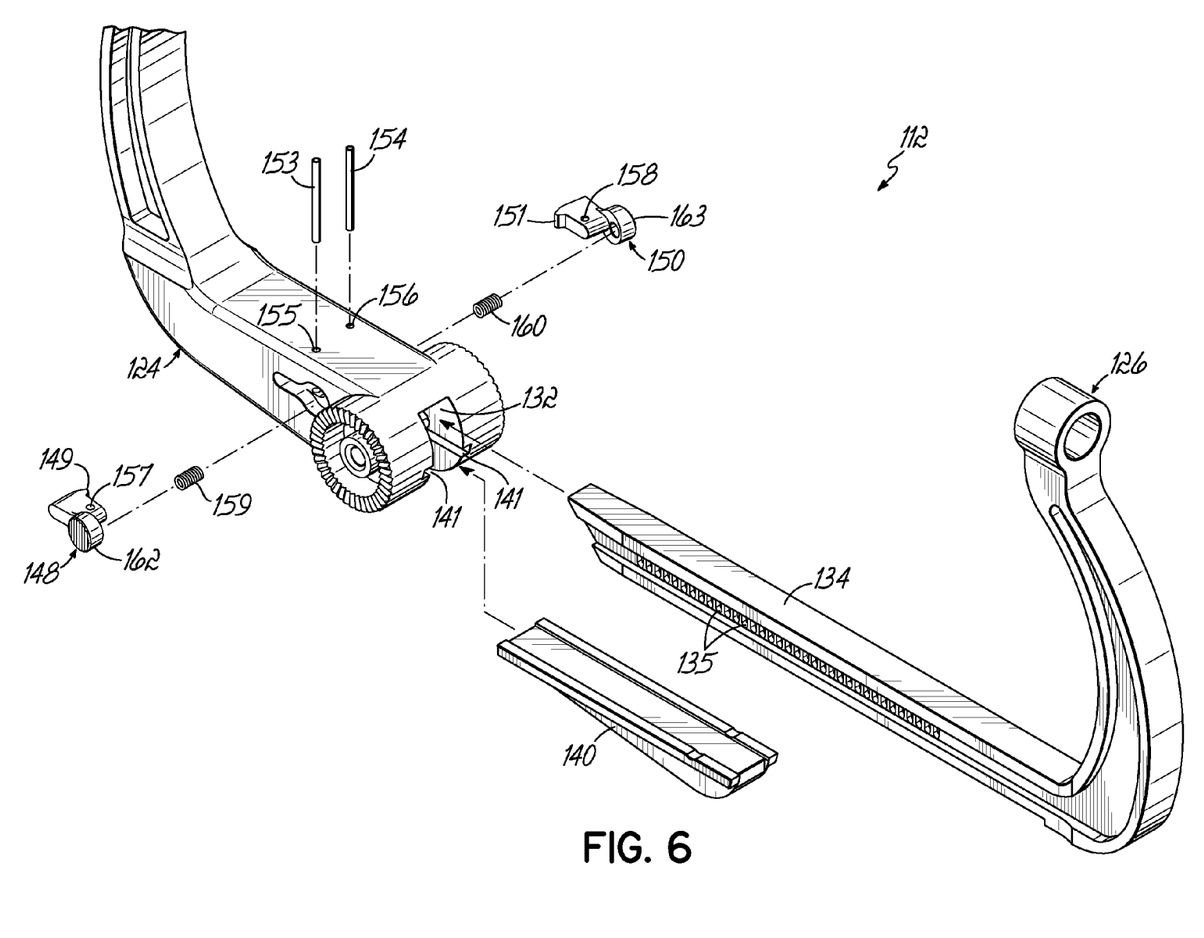
FIG. 6 is a disassembled perspective view of a skull clamp constructed in accordance with a second preferred embodiment of the disclosure, using a completely removable plate and two opposing pawls that cooperate with corresponding rows of opposing ratchet teeth.
Figure 7:
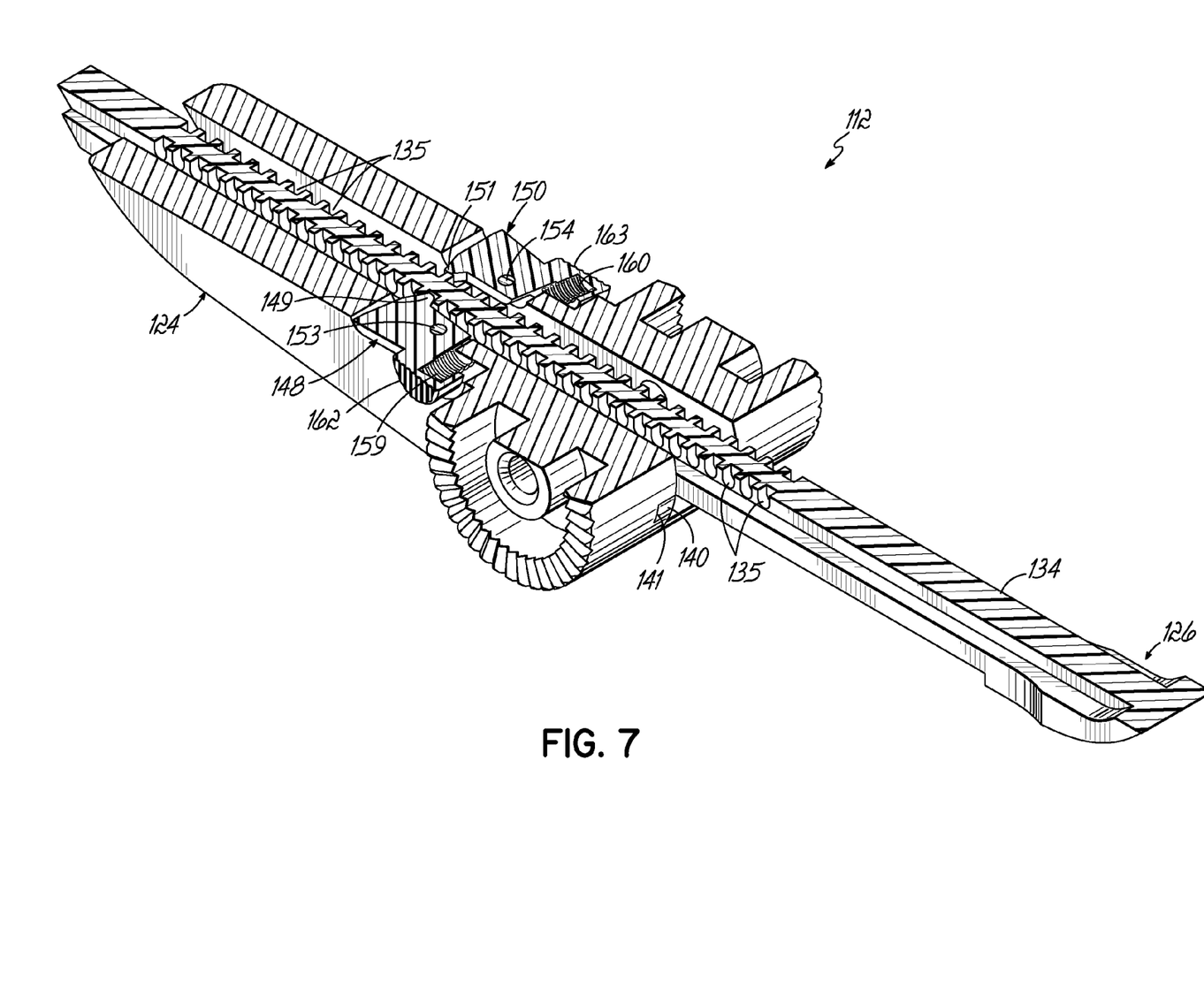
FIG. 7 is a perspective view, in cross section, of a portion of the skull clamp 112 shown in FIG. 6, with a pair of opposing pawls engaging opposing rows of ratchet teeth.
Figures 8A, 8B:
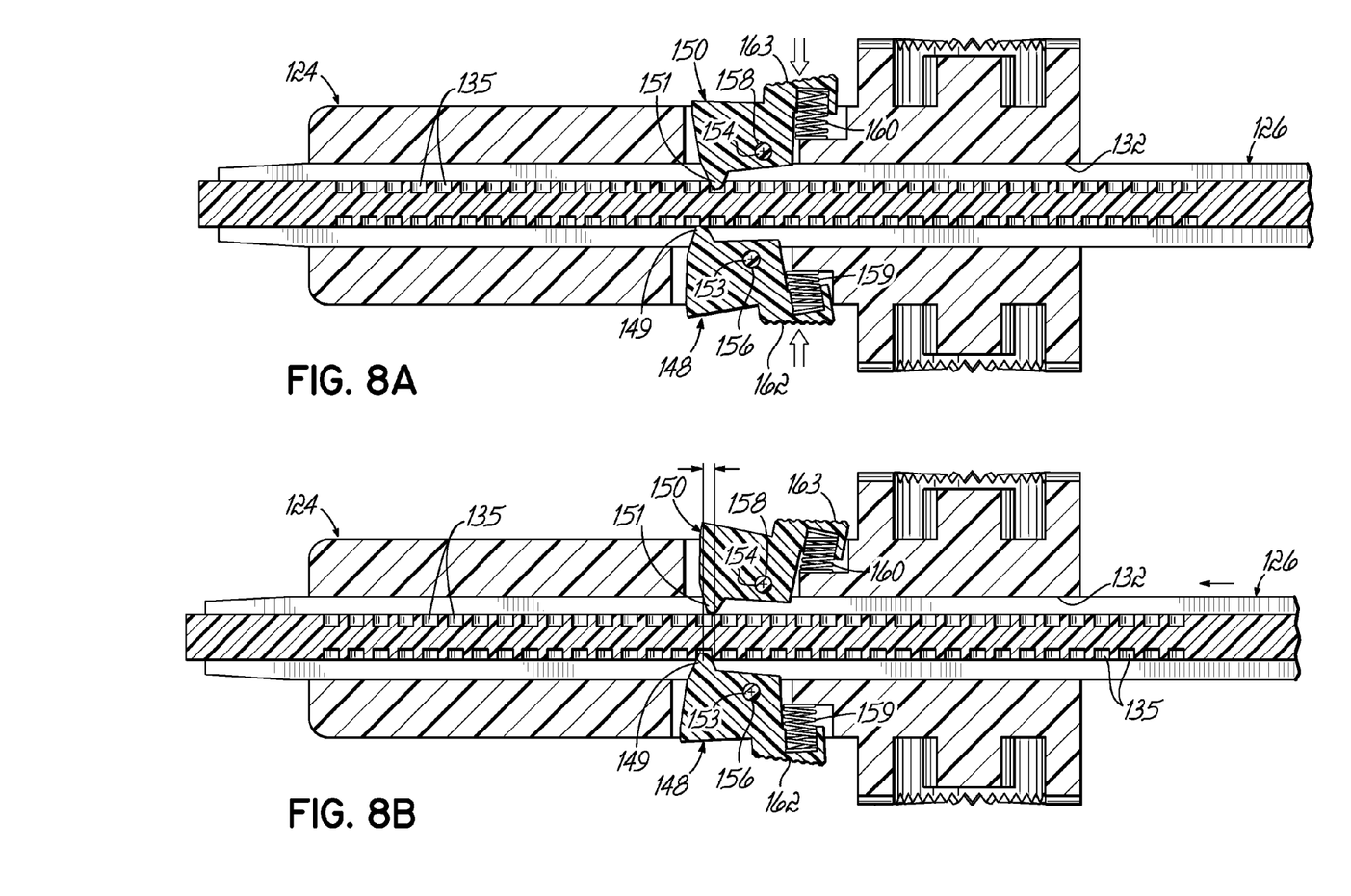
FIGS. 8A and 8B each show a top view, in section, of a portion of the structure shown in FIG. 7.

FIGS. 6, 7, and 8 show another preferred embodiment of the disclosure with respect to the cleaning and inspection feature, and also with respect to the adjustability feature of the clamp 112. More particularly, FIG. 6 shows the same generally U-shaped frame defined by base piece 124 and ratchet piece 126. Base piece 124 includes a slot 132 sized to receive a ratchet arm 134 of ratchet piece 126. The ratchet arm 134 includes a set of ratchet teeth 135 located along at least one of its sides. FIGS. 7 and 8 also show that ratchet arm 134 includes an opposing or opposite set of ratchet teeth 135 located on the opposite side.

A plate 140 removably connects to the base piece 124 to allow an operator to either open up or close off access to the slot 132. Preferably, opposing channels 141 formed in the base piece 124 are sized to receive the outer edges of the plate 140, in a slidable motion. Thus, in contrast to plate 40 (shown in the other FIGS, which hingedly connects to base piece 24), the plate 140 shown in FIGS. 6, 7, and 8 is completely removable from base piece 124, by sliding along opposing channels 141. With the plate 140 removed from the channels 141, the slot 132 is accessible, to facilitate inspection and cleaning of the inside surfaces thereof.

FIG. 6 also shows a first pawl 148 with at least one first engagement tooth 149, and a second pawl 150 with at least one second engagement tooth 151. The first and second pawls 148, 150, respectively, rotatably mount to the base piece 124 via pins 153 and 154, which extend into openings 155 and 156 formed in the base piece 124, respectively, and then into openings 157 and 158 formed in the first pawl 148 and the second pawl 150, respectively. Springs 159 and 160 bias the first pawl 148 and the second pawl 150, respectively, into engagement with the ratchet arm 134.

This can be seen more clearly in FIG. 7, which also shows the two opposing sets of ratchet teeth 135 on ratchet arm 134. More specifically, FIG. 7 shows how the at least one first engagement tooth 149 engages the ratchet teeth 135 on one side of the ratchet arm 134, while the at least one second engagement tooth 151 engages the ratchet teeth 135 on an opposite side of the ratchet arm 134. The springs 159 and 160 rotatably bias the first pawl 148 and the second pawl 150, respectively, into engagement with the ratchet arm 134, via rotational bias about axes 153, and 154. This relationship can be shown more clearly in FIGS. 8A and 8B.

FIG. 8 also shows the offset relationship of first pawl 148 with respect to second pawl 150, for the embodiment shown in FIGS. 6, 7, and 8. More particularly, pawls 148 and 150 do not reside in the same transverse plane. But as a further alternative, the first and second pawls 148, 150 could be aligned in the same transverse plane, but with the ratchet teeth 135 on opposite sides of the ratchet arm 134 providing the offset.

Moreover, and as yet another variation of this embodiment, the first pawl 148 and second pawl 150 could be located on the same side of the base piece 124, with the ratchet teeth 135 located on only one side of the ratchet arm 134. Nonetheless, there may be some preference for locating the first pawl 148 and the second pawl 150 on opposite sides of the base piece 124.

More particularly, the first pawl 148 includes an outer button surface 162, while second pawl 150 includes a similar outer button surface 163. These pushbutton surfaces 162, 163 can be pushed by an operator against the force of the springs 159, 160, respectively, to overcome the biasing force, and to thereby move the at least one first engagement tooth 149 and the at least one second engagement tooth 151, respectively, from engagement with the ratchet teeth 135, thereby to enable the ratchet arm 134 to be removed from the slot 132. With these pushbuttons 162 and 163 located on opposite sides of the base piece 124, it may be easier for an operator to simultaneously push two buttons at one time, to overcome the biasing force that causes the engagement teeth to engage the ratchet teeth 135 of the ratchet arm 134. Also, by having two separate mechanical structures that need to be acted on simultaneously by the operator and on opposite sides, this structure may provide an added degree of security, in that ratchet arm 134 may be less likely to be pulled inadvertently out of slot 132.

It should be understood that these Figures and this detailed description represent several preferred embodiments which exemplify the present invention. Those skilled in the art will readily appreciate that one or more modifications could be made to the structures shown and described herein, without departing from the principles of the invention. In that respect, each of the exemplary embodiments shown and described is meant to represent merely one subset of the subject matter covered by the broader claims appended to the end of this application. And rather than the Figures and this description, it is the appended claims which set forth the scope of the exclusionary right which the applicant seeks with respect to this application.

I claim:

1. A skull clamp for supporting a patient's head, comprising:
   a frame by a base piece having a slot formed therein and a ratchet extension piece with a ratchet arm extendable into the slot, the ratchet arm including ratchet teeth enageable by the base piece; and
   a plate hingedly connected to the base piece adjacent the slot, and operable to be hingedly moved between closed and open positions to close off and to open up access to the slot, respectively, thereby to facilitate cleaning and inspection of the slot.

2. The skull clamp of claim 1 farther comprising:
   a pin connected to the base piece, the plate hingedly connected to the pin for hinged movement between the open and closed positions.

3. The skull clamp of claim 2 further comprising:
   a plunger carried by the plate; and
   a first pawl mounted to the base piece and operatively connected to the plunger so as to be biased into engagement with at least one of the ratchet teeth of the ratchet arm, thereby to permit the ratchet arm to move further into the slot, but to prevent the ratchet arm from being removed therefrom;
   the plunger being retractable relative to the base piece to move the first pawl out of biased engagement with the ratchet teeth, to enable the ratchet arm to be withdrawn from the slot.

4. The skull clamp of claim 3 further comprising:
   the first pawl being mounted to the base piece, and having at least one first engagement tooth that is shaped complementary to the ratchet teeth, and with the same pitch; and
   a second pawl located adjacent the first pawl and also mounted to the base piece, the second pawl having at least one second engagement tooth that is shaped complementary to the ratchet teeth, with the same pitch, the second pawl also operatively connected to the plunger and biased into engagement with the ratchet teeth, thereby to permit the ratchet teeth and the ratchet arm to move further into the slot, but to prevent the ratchet arm from being moved outwardly therefrom;
   the at least one first engagement tooth and the at least one second engagement tooth being offset by a predetermined distance that is less than the pitch of the ratchet teeth, whereby the at least one first engagement tooth and the at least one second engagement tooth engage the ratchet teeth of the ratchet arm at different positions when the ratchet arm moves into the slot a distance equal to the pitch, thereby to permit additional engagement positions of the ratchet piece and the base piece so as to facilitate positioning the skull clamp relative to a patient.

5. The skull clamp of claim 4 wherein the predetermined distance is about half the pitch of the ratchet teeth.

6. The skull clamp of claim 4 and further comprising:
   a pin held by the base piece and hingedly connecting the plate to the base piece, the first and second pawls being rotatably mounted to the base piece and rotatable about the pin.

7. The skull clamp of claim 6 wherein at least one of the first pawl and the second pawl includes a spring that biases the pawl into engagement with the ratchet teeth.

8. The skull clamp of claim 7 wherein the spring is an arm integral with said at least one of the first pawl and the second pawl.

9. The skull clamp of claim 4 wherein the first pawl and the second pawl are located side by side and are about equal in length, with the at least one first engagement tooth comprising two first engagement teeth and the at least one second engagement tooth also comprising two second engagement teeth.

10. The skull clamp of claim 4 wherein the components thereof are made of radiolucent material.

11. The skull clamp of claim 2 wherein the plate is shaped so as to prevent hinged movement to an open position when the ratchet arm is in the slot.

12. The skull clamp of claim 1 wherein the plate has first and second ends and is hingedly connected to the base piece at the first end, the second end thereof including an arcuately shaped cut-out region to facilitate hinged movement of the plate relative to the base piece.

13. The skull clamp of claim 1 wherein the frame is U-shaped.

14. A skull clamp for supporting a patient's head, comprising:
    a frame defined by a base piece having a longitudinal slot formed therein and a ratchet extension piece with a ratchet arm extendable into the longitudinal slot along a first linear direction, the ratchet arm including ratchet teeth engageable by the base piece;
    a plunger carried by the base piece; and
    a first pawl mounted to the base piece and operatively connected to the plunger so as to be biased into engagement with at least one of the ratchet teeth of the ratchet arm, thereby to permit the ratchet arm to move further into the slot along the first linear direction, but to prevent the ratchet arm from being removed therefrom, the plunger being retractable relative to the base piece to move the first pawl out of biased engagement with the ratchet teeth, to enable the ratchet arm to be withdrawn from the slot, he first pawl being mounted to the base piece, and having at least one first engagement tooth that is shaped complementary to the ratchet teeth, and with the same pitch; and
    a second pawl separate from the first pawl and also mounted to the base piece, the second pawl having at least one second engagement tooth that is shaped complementary to the ratchet teeth, with the same pitch, the second pawl also operatively connected to the plunger and biased into engagement with the ratchet teeth, thereby to permit the ratchet arm to move further into the slot along the first linear direction, but to prevent the ratchet arm from being moved outwardly therefrom;
    the at least one first engagement tooth and the at least one second engagement tooth being offset by a predetermined distance that is less than the pitch of the ratchet teeth, whereby the at least one first engagement tooth and the at least one second engagement tooth engage the ratchet teeth of the ratchet arm at different positions when the ratchet arm moves into the slot a distance equal to the pitch, thereby to permit additional engagement positions of the ratchet piece and the base piece along the first linear direction so as to facilitate positioning the skull clamp relative to a patient.

15. The skull clamp of claim 14 and further comprising:
a plate hingedly connected to the base piece, the plate hingedly moveable between closed and open positions to close off and to open up access to the slot, respectively, thereby to facilitate cleaning and inspection of the slot, the plunger carried by the plate.

16. The skull clamp of claim 15 and further comprising:
a pin held by the base piece and hingedly connecting the plate to the base piece, the first and second pawls being rotatably mounted to the base piece and rotatable about the pin.

17. The skull clamp of claim 16 wherein at least one of the first pawl and the second pawl includes a spring that biases the pawl into engagement with the ratchet teeth.

18. The skull clamp of claim 17 wherein the spring is an arm integral with, said at least one of the first pawl and the second pawl.

19. The skull clamp of claim 14 wherein the predetermined distance is about half the pitch of the ratchet teeth.

20. The skull clamp of claim 14 wherein the frame is U-shaped.

21. A skull clamp for supporting a patient's head, comprising:
a frame defined by a base piece having a longitudinal slot formed therein and a ratchet extension piece with a ratchet arm extendable into the longitudinal slot along a first linear direction, the ratchet arm including at least one row of ratchet teeth engageable by the base piece;
a first pawl mounted to the base piece and having at least one first engagement tooth that is shaped complementary to the ratchet teeth, and with the same pitch, the at least one first engagement tooth of the first pawl being biased into engagement with at least one of the ratchet teeth of the ratchet arm, thereby to permit the ratchet arm to move further into the slot along the first linear direction, but to prevent the ratchet arm from being removed therefrom; and
a second pawl separate from the first pawl and mounted to the base piece and having at least one second engagement tooth that is shaped complementary to the ratchet teeth, with the same pitch, the at least one second engagement tooth of the second pawl being biased into engagement with the ratchet teeth, thereby to permit the ratchet arm to move further into the slot along the first linear direction, but to prevent the ratchet arm from being moved outwardly therefrom;
the at least one first engagement tooth and the at least one second engagement tooth being offset by a predetermined distance that is less than the pitch of the ratchet teeth, whereby the at least one first engagement tooth and the at least one second engagement tooth engage the ratchet teeth of the ratchet arm at different positions when the ratchet arm moves into the slot a distance equal to the pitch, thereby to permit additional engagement positions of the ratchet piece and the base piece along the first linear direction so as to facilitate positioning the skull clamp relative to a patient.

22. The skull clamp of claim 21 wherein the ratchet arm includes two rows of oppositely directed ratchet teeth, and the first and second pawls are located on opposite sides of the base piece, such that the first and second paws engage Opposite sides of the ratchet arm.

23. The skull clamp of claim 21 wherein the first and second pawls further comprise, respectively, first and second pushbutton/spring mechanisms, each pushbutton/spring mechanism being manipulatable by an operator to overcome the biasing engagement of the respective at least one first or second engagement tooth, thereby to enable the ratchet arm to be removed from the base piece.

24. The skull clamp of claim 21 further comprising:
a plate removably connected to the base piece along the first linear direction, thereby to enable access to the to facilitate inspection and cleaning thereof.

25. The skull clamp of claim 24 wherein the base piece has opposing channels formed therein adjacent the slot and extending along the first linear direction, the plate removably connected to the base piece along the first linear direction and via the channels.

* * * * *

UNITED STATES PATENT AND TRADEMARK OFFICE
CERTIFICATE OF CORRECTION

PATENT NO. : 9,681,924 B2  
APPLICATION NO. : 12/749926  
DATED : June 20, 2017  
INVENTOR(S) : Sean Rolfes Page 1 of 1

It is certified that error appears in the above-identified patent and that said Letters Patent is hereby corrected as shown below:

In the Specification

Column 1, Line approx. 45, reads "... ratchet aim to prevent it from backing out" should read --... ratchet arm to prevent it from backing out--.

Column 4, Line approx. 48, reads "... the first end second pawls." should read --... the first and second pawls.--.

Column 4, Line approx. 65-66, reads "... According to the arrangement of components shown in FIG. 1, in additional to the skull clamp 12, ..." should read --... According to the arrangement of components shown in FIG. 1, in addition to the skull clamp 12, ...--.

Signed and Sealed this  
Twelfth Day of September, 2017

Joseph Matal  
*Performing the Functions and Duties of the*  
*Under Secretary of Commerce for Intellectual Property and*  
*Director of the United States Patent and Trademark Office*